(12) United States Patent
Webb

(10) Patent No.: US 6,174,321 B1
(45) Date of Patent: Jan. 16, 2001

(54) COLLAGEN FORCEPS

(75) Inventor: Nicholas J. Webb, Wrightwood, CA (US)

(73) Assignee: Eagle Vision, Inc., Memphis, TN (US)

( * ) Notice: Under 35 U.S.C. 154(b), the term of this patent shall be extended for 0 days.

(21) Appl. No.: 09/310,061

(22) Filed: May 11, 1999

Related U.S. Application Data

(63) Continuation-in-part of application No. 08/907,199, filed on Aug. 6, 1997, now Pat. No. 5,921,990.

(51) Int. Cl.$^7$ ................................................... H61B 17/50
(52) U.S. Cl. ........................................ 606/210; 606/205
(58) Field of Search .............................. 606/210, 205, 606/206, 207, 208, 209, 211; D28/55; D24/143

(56) References Cited

U.S. PATENT DOCUMENTS

| | | | |
|---|---|---|---|
| 1,119,532 | * 12/1914 | Parks | 606/207 |
| 1,433,340 | * 10/1922 | Clark | 606/211 |
| 4,257,406 | 3/1981 | Schenk | 128/20 |
| 4,726,367 | 2/1988 | Shoemaker | 128/303 R |
| 5,015,252 | 5/1991 | Jones | 606/205 |
| 5,019,091 | 5/1991 | Porat et al. | 606/205 |
| 5,156,431 | 10/1992 | Lowe | 294/99.2 |
| 5,176,696 | 1/1993 | Saunders | 606/174 |
| 5,178,622 | 1/1993 | Lehner, II | 606/107 |
| 5,217,464 | 6/1993 | McDonald | 606/107 |
| 5,292,324 | 3/1994 | McDonald | 606/107 |
| 5,556,403 | 9/1996 | Michalos | 606/148 |
| 5,630,821 | 5/1997 | Klaas | 606/107 |
| 5,792,137 | 8/1998 | Carr et al. | 606/29 |

FOREIGN PATENT DOCUMENTS

0177252 * 4/1986 (EP) .................................... 606/207

* cited by examiner

Primary Examiner—Michael Buiz
Assistant Examiner—Lien Ngo
(74) Attorney, Agent, or Firm—David P. Gordon; David S. Jacobson; Thomas A Gallagher

(57) ABSTRACT

The collagen forceps includes two elongate members coupled at a proximal live hinge. The elongate members are each provided with a knurled finger pad ergonomically contoured to stably receive a finger or thumb of a physician, and a manipulation tip having an interior collagen rod gripping surfaces. The manipulation tip of the collagen forceps includes two gripping channels preferably oriented substantially orthoganally relative to each other. In addition, the manipulation tip is preferably angled relative to an axis of the collagen forceps. The proximal end of the forceps includes a shaft which is also preferably angled relative to the axis, and thereby facilitates grip and balance of the collagen forceps in the hand of the physician.

16 Claims, 4 Drawing Sheets

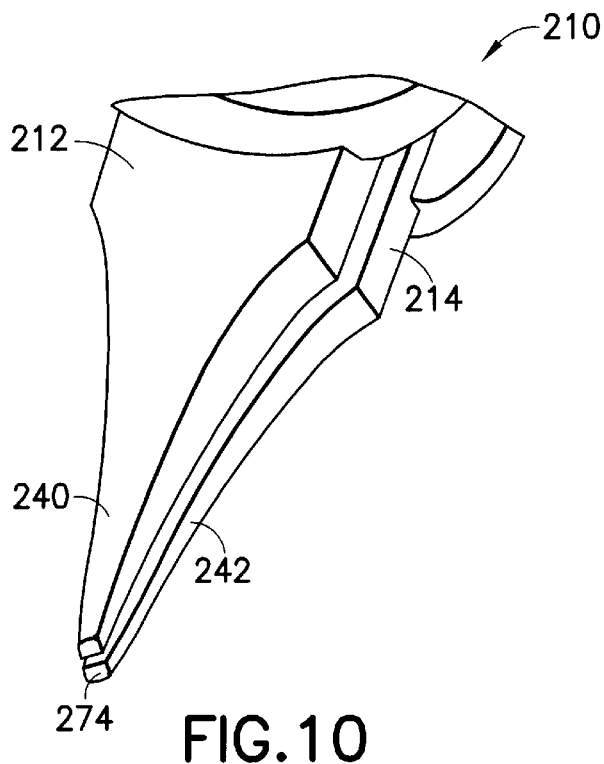
FIG.10
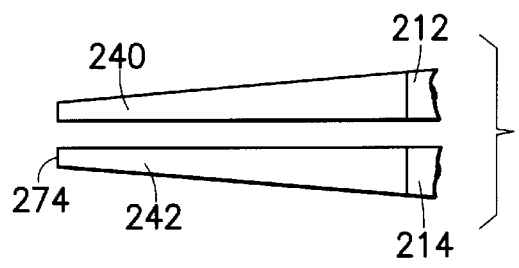
FIG.11
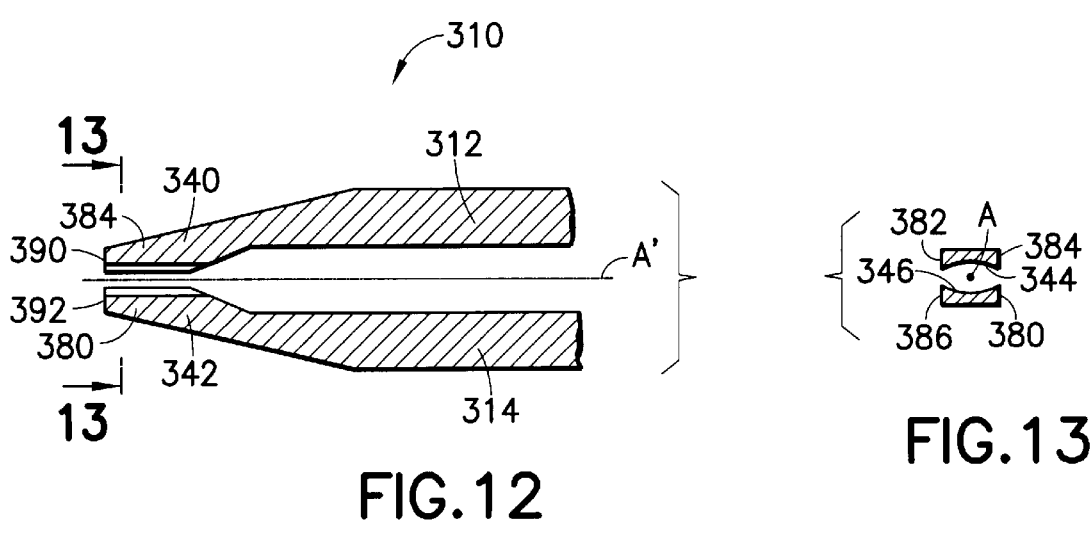
FIG.12
FIG.13

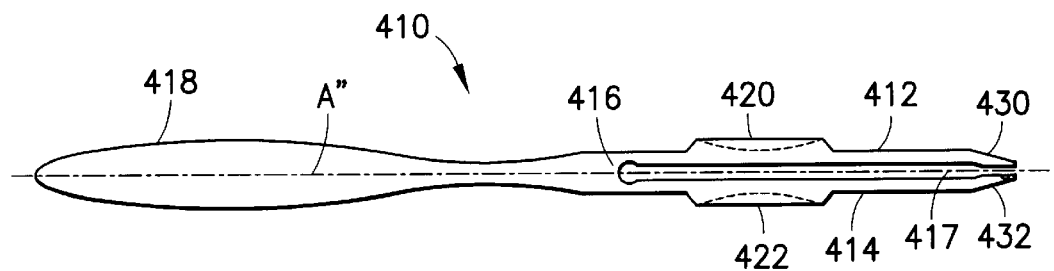
FIG.14
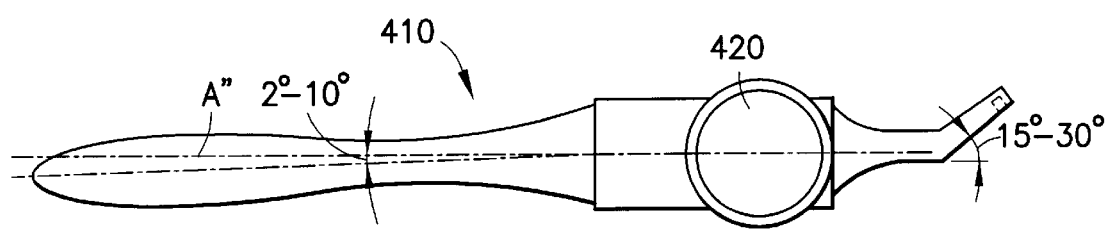
FIG.15
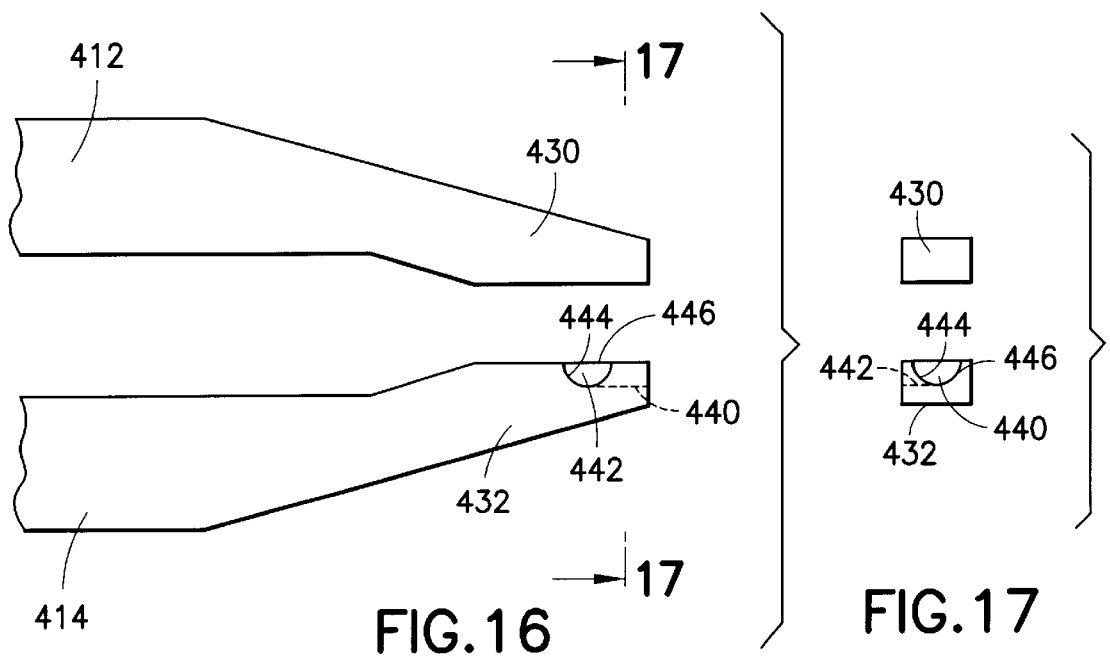
FIG.16
FIG.17

COLLAGEN FORCEPS

This application is a continuation-in-part of U.S. Ser. No. 08/907,199 now U.S. Pat. No. 5,921,990, filed Aug. 6, 1997, which is hereby incorporated by reference herein in its entirety.

BACKGROUND OF THE INVENTION

1. Field of the Invention

This invention relates broadly to ophthalmological instruments. More particularly, this invention relates to instruments used to insert collagen rods into the punctal opening.

2. State of the Art

A variety of eye problems are related to an insufficient volume of tears on the surface of the eyes. The most common is keratoconjunctivitis sicca, also known as dry eyes. Contact lens problems are also often provoked by a lack of tear volume. A common cause for the insufficient tear volume is the drainage of tear fluid through the punctal opening of the nasal lacrimal duct and into the nasal passage, thereby removing the fluid from where it is needed at the eye surface. Furthermore, drainage of tear fluid through the nasal lacrimal duct into the nasal passage is believed to be the cause or associated with several additional problems such as post nasal drip, sinusitis, allergies, headaches, and snoring.

A number of methods for closing the punctal opening have been used to prevent drainage of tears through the nasal lacrimal duct, including suturing, laser sealing, and plugging. However, before any of the above methods are used on a patient, small collagen rods are often implanted into the punctal openings in the eyes of the patient to occlude the nasal lacrimal ducts. The physician treating the patient can then better diagnose the patient. The collagen rod implants slowly dissolve in about a week, giving the physician ample time to verify the potential clinical benefits of more permanent occlusion for a particular patient, and also to evaluate receptivity of the patient to duct occlusion.

The collagen rods intended for occluding the nasal lacrimal ducts are extremely small (approximately 2 mm in length and having a diameter of approximately 0.2 mm). Because of the small size of the collagen rods, a tool is required to insert the rods into the punctal opening. Referring now to prior art FIG. 1, the tool of the prior art used to insert collagen rods is typically a straight collagen forceps 10, the shape and size of a conventional tweezers. The collagen forceps has two arms 12, 14 resiliently hinged at a proximal portion 16 and terminating distally in two elongate tips 18, 20. Each tip has an inner flat surface 22, 24 which grips the collagen rod. The arms 12, 14, which are held by the physician, are relatively narrow and do not provide comfortable and stable finger and thumb grips. Comfortable and stable finger and thumb grips are desirable when working with very small implants close to the eye, as fine manipulation of the elongate tips is required to implant the rods into the punctal openings of the eyes. Additionally, the inner gripping surfaces 22, 24 are inadequate for gripping cylindrical collagen rods as the rods tend to slip against and rotate on the flat surface. Furthermore, prior art forceps instruments are unable to provide pre-insertion dilation of the punctal opening, nor do they have the ability to push the collagen rod into the punctal opening such that the collagen rod is pushed below the punctal opening. A second instrument is required for those purposes.

SUMMARY OF THE INVENTION

It is therefore an object of the invention to provide a collagen forceps designed to easily insert a collagen rod into the punctal opening.

It is another object of the invention to provide a collagen forceps which is comfortable to hold and which thereby permits easy and fine manipulation of the collagen rods.

It is also an object of the invention to provide a collagen forceps which can securely grip the collagen rod.

It is an additional object of the invention to provide a collagen forceps which can grip the collagen rod in two substantially orthogonally orientations.

It is also an object of the invention to provide a collagen forceps having the ability to predilate the punctal opening.

It is another object of the invention to provide a collagen forceps having which can be used to fully insert collagen rods beneath the punctal opening.

In accord with these objects which will be discussed in detail below, a collagen forceps is provided. According to the invention, the collagen forceps generally includes two elongate members coupled at a proximal live hinge. The elongate members are each provided with a knurled finger pad ergonomically contoured to stably receive a finger or thumb of a physician, and a manipulation tip having an interior collagen rod gripping surface.

According to a first embodiment of the invention, the gripping surfaces of each elongate member includes an angulated or curved concave surface shaped to engage the collagen rod axially and is preferably provided with rod engagement ridges. Preferably each manipulation tip is also provided with a silicon boot. In addition, the proximal end of the instrument is provided with a projection having a dilation/insertion tip.

The contoured finger pads provide a physician with a comfortable and controllable instrument. The gripping surfaces of the manipulation tips, especially when provided with silicon boots, permit easy grasping of the collagen rods and stably engage the rods such that the collagen rod cannot rotate about or slide away from the gripping surfaces. As such, the collagen forceps permits relatively easy manipulation of the rods into the ducts. In addition, the dilation/insertion tip of the projection can be used to dilate the punctal opening prior to collagen rod insertion therein, and may also be used after the insertion of the collagen rod to push the collagen rod deeper into the punctal opening.

According to second, third, and fourth embodiments, dilation/insertion means are provided at the distal end of the instrument on one or both of the elongate members.

According to a fifth embodiment of the invention, the manipulation tip of the collagen forceps includes two gripping channels preferably oriented substantially orthogonally relative to each other. In addition, the manipulation tip is preferably angled relative to an axis of the collagen forceps. The proximal end of the forceps includes a shaft which is also preferably angled relative to the axis, preferably in a direction opposite the manipulation tips, and facilitates the grip and balance of the collagen forceps in the hand of the physician.

Each embodiment of the collagen forceps of the invention enables a controlled implantation of collagen rods through the punctal opening and into the naso-lacrimal duct.

Additional objects and advantages of the invention will become apparent to those skilled in the art upon reference to the detailed description taken in conjunction with the provided figures.

BRIEF DESCRIPTION OF THE DRAWINGS

FIG. 10 is an enlarged broken perspective view of a third embodiment of a collagen forceps according to the invention;

FIG. 11 is enlarged broken side elevation view of the collagen forceps of FIG. 10;

FIG. 12 is an enlarged broken side elevation view of a fourth embodiment of a collagen forceps according to the invention;

FIG. 13 is a cross-section through line 13—13 in FIG. 12;

FIG. 14 is a side elevation of a fifth embodiment of the collagen forceps according to the invention;

FIG. 15 is a top view of the fifth embodiment of a collagen forceps according to the invention;

FIG. 16 is an enlarged side elevation of the distal end of the fifth embodiment of the collagen forceps according to the invention; and FIG. 17 is a cross-section through line 17—17 in FIG. 16.

DETAILED DESCRIPTION OF THE PREFERRED EMBODIMENTS

Figure 1:
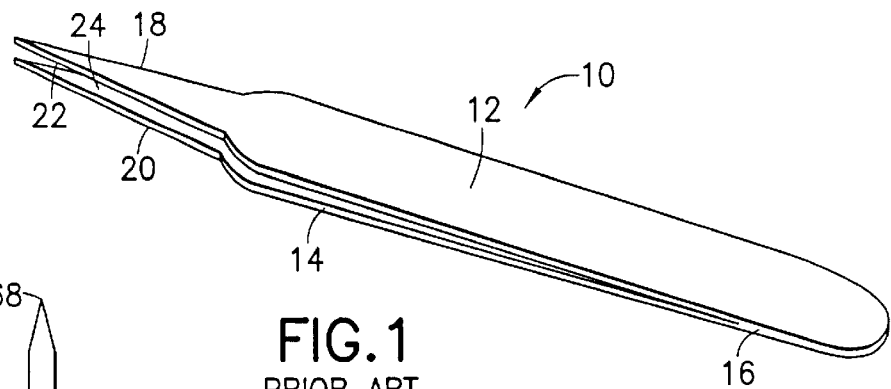
FIG. 1 is a prior art collagen forceps.
Figure 2:
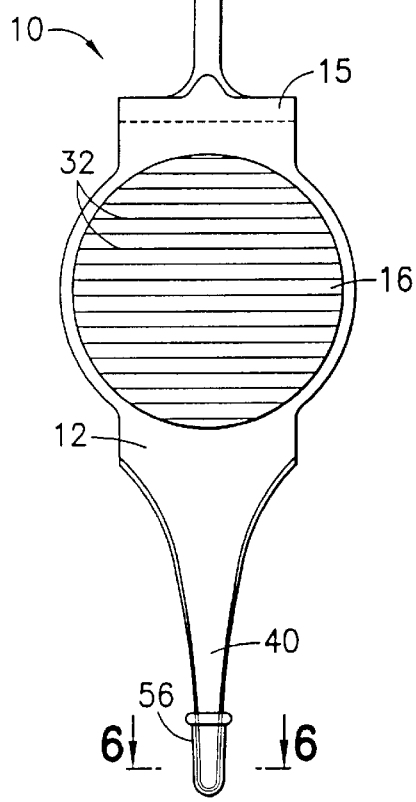
FIG. 2 is top view of the collagen forceps of the invention.
Figure 4:
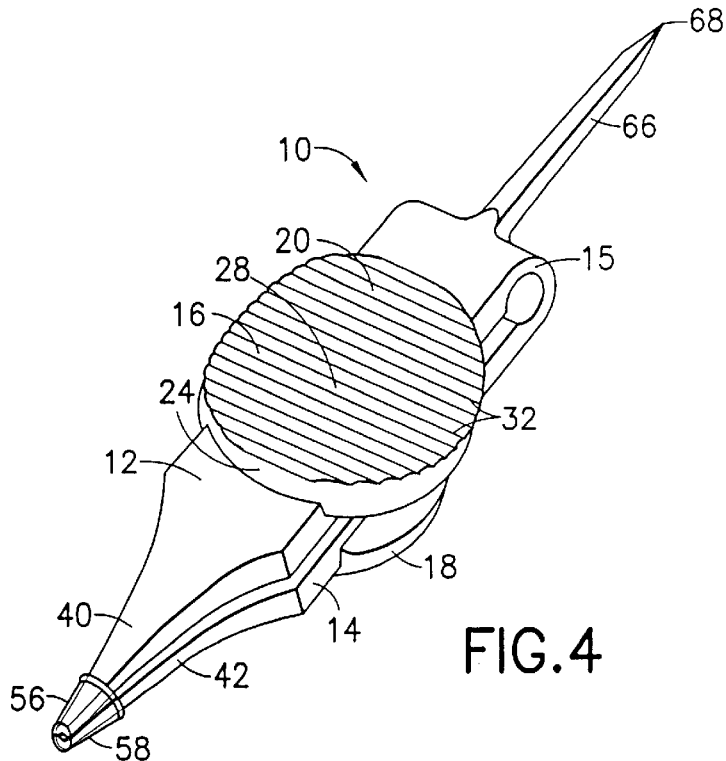
FIG. 4 is a perspective view of the collagen forceps shown in FIG. 2.
Figure 3:
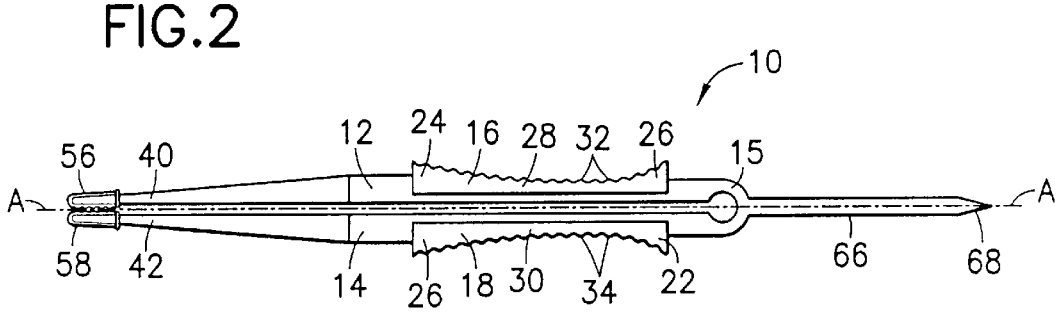
FIG. 3 is a side elevation view of the collagen forceps shown in FIG. 2.
Figure 5:
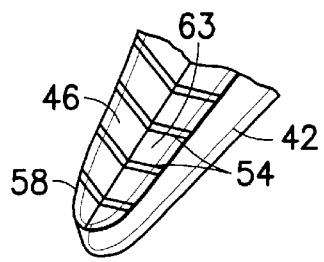
FIG. 5 is an enlarged broken perspective view of a distal tip of the collagen forceps shown in FIG. 4.
Figure 6:
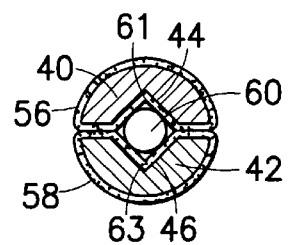
FIG. 6 is an enlarged side elevation of the boot of the collagen forceps of the invention.

Turning now to FIGS. 2 through 4, a collagen forceps 10 according to a first embodiment of the invention is shown. The collagen forceps 10 includes first and second elongate members 12, 14 coupled at a live hinge 15. The elongate members 12, 14 are preferably substantially parallel, and provided with a small separation from each other along their length. Each elongate member 12, 14 is provided with a finger pad 16, 18 which is preferably round or oval in shape. The finger pads 16, 18 are preferably wider than the width of the elongate members on either side of the finger pads. The first finger pad 16 is preferably ergonomically contoured to comfortably receive one or more fingers of a physician, while the second finger pad 18 is preferably contoured to receive a thumb of the physician. A preferred contour of the first and second finger pads provides raised rear portions 20, 22 and front portions 24, 26 and relatively depressed central portions 28, 30. In addition, the finger pads 16, 18 are preferably provided with traction ridges 32, 34 (knurls) which are engaged by the finger(s) and thumb, and to prevent the finger(s) and thumb from slipping off the finger pads. The traction ridges are oriented substantially perpendicular to the longitudinal axis A of the forceps.

Figure 7:
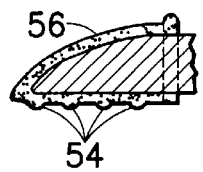
FIG. 7 is an enlarged cross-section across line 6—6 in FIG. 1, with the collagen forceps holding a collagen rod.

Referring now to FIGS. 2 through 6, each elongate member 12, 14 is also provided with a manipulation tip 40, 42 having an interior collagen rod gripping surface 44, 46. The gripping surfaces 44, 46 are preferably angulated or curved concave surfaces shaped to engage a collagen rod 60 axially within a groove 61, 63 formed by the surfaces (FIG. 6); i.e., the gripping surfaces engage the collagen rod at more than two lines of contact. Preferably each manipulation tip 40, 42 is also provided with a thin, flexible, silicon boot 56, 58 (FIG. 7) preferably provided with engagement ridges 54 which securely grip and hold the collagen rod. The boots 56, 58 are shaped to fit snugly over, and preferably contour to, the manipulation tips 40, 42 (FIGS. 2–4 and 6), and provide a high friction surface for easily gripping collagen rods. The silicon boots are preferably made from a 60 Durometer silicon.

Turning back to FIGS. 2 through 4, a projection 66 is provided adjacent the hinge 15 and is preferably directed in a direction opposite the elongate members 12, 14. The projection 66 includes a preferably tapered dilation/insertion tip 68.

In practice, the physician, preferably first inserts the dilation/insertion tip 68 of the projection 66 through the punctal opening to dilate the punctal opening. The physician then turns the instrument such that the tips 40, 42 are distally directed, and places one or two fingers on one finger pad 16, and a thumb on the other finger pad 18. When pressure by the physician's finger(s) and thumb on the finger pads is not substantial enough to move the manipulation tips 40, 42 toward each other, a space is provided between the tips for picking up a collagen rod. With light pressure on the finger pads, the physician is able to move the tips toward each other to securely grab a collagen rod from a working surface. As stated above, the boots 56, 58, if provided, assist in picking up and gripping a collagen rod. In addition, the contoured finger pads 16, 18 and traction ridges 32, 34 provide comfort to the physician and enable subtle control of the collagen forceps.

With a collagen rod being axially held by the gripping surfaces 44, 46, i.e., with the gripping surfaces gripping the collagen rod around its circumference, the physician manipulates the collagen rod into the dilated punctal opening. After pushing the collagen rod as deep as possible via manipulation of the tips 40, 42, the physician releases pressure on the finger pads 16, 18 to permit the tips to move apart and release the collagen rod from the gripping surfaces. If desired, the physician then turns the collagen forceps 10 around, and using the dilation/insertion tip 68 of the projection 66 further pushes the collagen rod into and below the punctal opening.

The collagen forceps is preferably molded from an acrylic plastic, providing an inexpensive and disposable instrument. The instrument may also be made from stainless steel, other metals, or other suitable medical grade materials.

By way of example, and with the understanding that other dimensions may also be used, dimensions for the collagen forceps of the first embodiment are hereby provided. The collagen forceps 10, from the manipulation tips 40, 42 to the dilation/insertion tip 68, has a length of approximately three inches. The finger pads 16, 18 each have a diameter of approximately three-quarter inches. The width of the elongate members 12, 14 on either side of the finger pads is approximately three-eighths inches. The projection 66 is approximately three-quarter inches in length and approximately 0.060 inches in diameter until it tapers to the dilation/insertion tip. The manipulation tips 40, 42 are approximately one inch in length, and have a gripping surface 44, 46 shaped to accommodate collagen rods having a diameter of approximately 0.2 mm to 0.6 mm.

Figure 8:
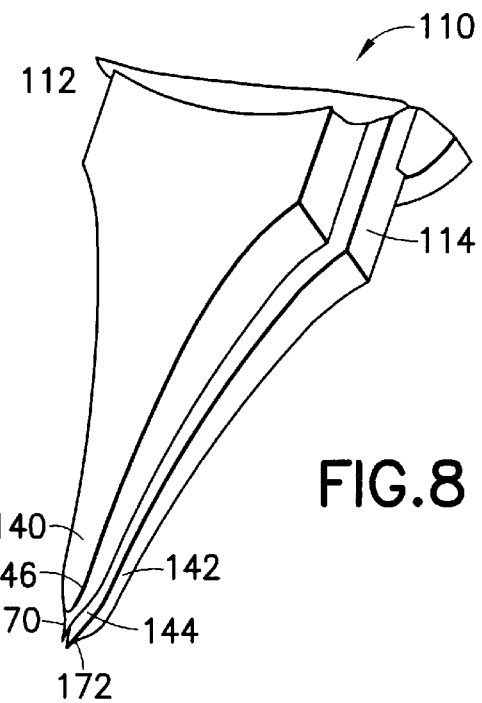
FIG. 8 is an enlarged broken perspective view of a second embodiment of a collagen forceps according to the invention.
Figure 9A:
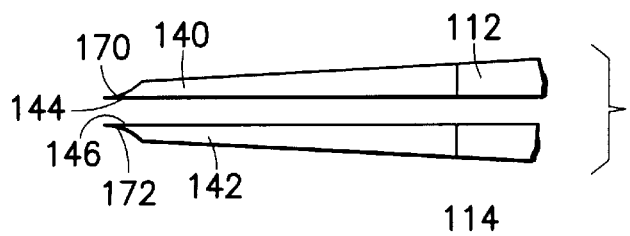
FIGS. 9A and 9B are enlarged broken side elevation views illustrating the collagen forceps of FIG. 8 in open and closed positions, respectively.
Figure 9B:
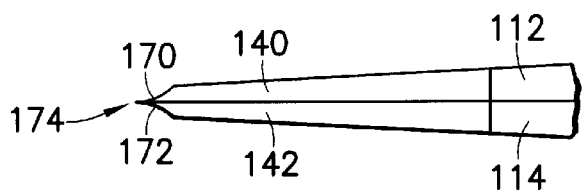

Turning now to FIG. 8, a second embodiment of a collagen forceps 110, substantially similar to the first embodiment (with like parts having numbers incremented by 100), is shown. Each elongate member 112, 114 is provided with a manipulation tip 140, 142 having an interior collagen rod gripping surface 144, 146. Each manipulation tip 140, 142 tapers toward the medial side of the respective tip (FIG. 9A), such that when the two tips 140, 142 are brought together in a closed position (FIG. 9B), a pointed dilator/inserter 174 is formed. The dilator/inserter 174 may be used in the same capacity as the dilation/insertion tip of the first embodiment.

Turning now to FIGS. 10 and 11, a third embodiment of a collagen forceps 210, substantially similar to the first embodiment (with like parts having numbers incremented by 200), is shown. Each elongate member 212, 214 is provided with a manipulation tip 240, 242. At least one manipulation tip 242 is provided with a dilator/insertion protuberance 274 extending distally from the manipulation tip. The dilator/inserter 274 may be used in the same capacity as the dilation/insertion tip of the first embodiment.

Turning now to FIGS. 12 and 13, a fourth embodiment of a collagen forceps 310, substantially similar to the first embodiment (with like parts having numbers incremented by 300), is shown. Each elongate member 312, 314 is provided with a manipulation tip 340, 342 having a curved interior collagen rod gripping surface 344, 346 which extends at lateral portions 380, 382, 384, 386 toward the longitudinal axis A" of the forceps. The manipulation tips at their most distal portions 390, 392 are sized, e.g, 0.06 inches across each manipulation tip and 0.01 inches down through the center of each manipulation tip, such that when they are brought together in a closed position, a dilator/inserter is formed.

Referring now to FIGS. 14 and 15, a fifth and currently preferred embodiment of a collagen forceps 410 is shown. The collagen forceps 410 includes first and second elongate members 412, 414 coupled at a live hinge 416. The elongate members 412, 414 are preferably substantially parallel, and provided with a small separation 417 from each other along their length. Each elongate member 412, 414 is provided with a contoured finger pad 420, 422, each preferably round or oval in shape and adapted to receive a finger or the thumb of a physician. A shaft 418 extends proximally from the hinge 416. The shaft 418 is preferably slightly laterally angled, e.g. 2°–10°, relative to the axis A" of the collagen forceps.

Referring now to FIGS. 14 through 17, each elongate member 412, 414 is also provided with a distal manipulation tip 430, 432. The manipulation tips 430, 432 are preferably angled laterally relative to the axis A", e.g, by 15°–30°, in a direction opposite the shaft 418. At least one manipulation tip 432 includes two channels 440, 442, which are each preferably substantially hemispherical in cross-section. One channel 440, an end channel, is preferably oriented along the axis of manipulation tip 432 and the other channel 442, a side channel, is preferably oriented substantially perpendicular thereto. Channel 440 includes a stop or closed end 444, and channel 442 includes a stop or end 446.

In use, the shaft 418 of the collagen forceps 410 in cradled in the palm of a physician, and the physician places his or her fingers and thumb on the finger pads 420, 422. The elongate shaft 418, angled relative to the axis A", enhances the comfort of the physician's grip of the forceps and also helps to balance the device. The collagen forceps may then be manipulated to pick up from a surface and hold a collagen rod in either the end channel 440 or the side channel 442.

If it is desired to hold a collagen rod in the end channel 440, the collagen forceps 410 is manipulated to pick up a collagen rod from a surface or from a vial such that the collagen rod is positioned at least partially within the end channel 440 and then the manipulation tip 430 is closed against the exposed side of the collagen rod. The exposed end of a collagen rod may be pushed against a surface to seat the rod within the length of the channel 440, with the stop 444 preventing further movement. It will be appreciated that the angle of the manipulation tips 430, 432 relative to the axis A" facilitates pushing the end of the collagen rod against a surface while eliminating potential physician hand strain from such movement.

If it is desired to hold a collagen rod in the side channel 442, the collagen forceps 410 is manipulated to position a collagen rod at least partially within the side channel 444 of manipulation tip 432, and then the manipulation tip 430 is closed against the exposed side of the collagen rod. The exposed end rod may be pushed against a surface to seat the rod within the length of the channel 442, with the stop 446 preventing further movement. Again, the angle of the manipulation tips 430, 432 facilitates such seating of the rod while permitting the hand of the physician to remain in an ergonomically preferred position.

In either the end channel or the side channel, the collagen rod is securely gripped along more than two longitudinal lines parallel to the longitudinal axis of the collagen rod.

The physician then manipulates the collagen rod into the dilated punctal opening. After pushing the collagen rod to a desired-depth via manipulation of the tips 430, 432, the physician releases pressure on the finger pads 420, 422 to permit the tips to move apart and release the collagen rod from the gripping surfaces.

There have been described and illustrated herein several embodiments of a collagen forceps. While particular embodiments of the invention have been described, it is not intended that the invention be limited thereto, as it is intended that the invention be as broad in scope as the art will allow and that the specification be read likewise. Thus, with respect to the fifth embodiment, while only one manipulation tip is shown as having a collagen rod channel, it will be appreciated that both manipulation tips may include contoured surfaces, e.g. channels, which alone or together which the contoured surfaces on the other tip are adapted to securely grip a collagen rod therein. In addition, while the manipulation tips and shaft have been shown and described as being angled at particular angles relative to axis A", it will be appreciated that the manipulation tips and shaft may be angled at other respective angles, or oriented axial with A". Also, with respect to all of the embodiments, while particular contours for a finger pad have been disclosed, it will be appreciated that other contours can be used as well. Furthermore while ridges or knurls have been disclosed on the finger pads, it will be understood other traction means, e.g., grooves, can be used as well. Moreover, while the traction ridges or knurls have been described as being oriented perpendicular to the longitudinal axis of the forceps, it will be appreciated that the knurls on one or both of the finger pads may be at an angle other than perpendicular to the axis. Also, while a live hinge has been disclosed for coupling the elongate members, another coupling means may be used. It will therefore be appreciated by those skilled in the art that yet other modifications could be made to the provided invention without deviating from its spirit and scope as so claimed.

What is claimed is:

1. A collagen forceps having a longitudinal axis, said collagen forceps for use by a practitioner to insert a collagen rod having a longitudinal axis into a punctal opening of an eye, comprising;

a) a first elongate member having a proximal portion and distal portion provided with a first end, said first end including a first collagen rod gripping means having first channel, a second collagen rod gripping means having a second channel angled relative to said first channel;

b) a second elongate member having a proximal portion and a distal portion provided with a second end; and c) coupling means for hingeably coupling said first and second elongate members, wherein the collagen forceps is adapted to permit the practitioner to releasably securably grip the collagen rod within at least one of said first and second channels of said collagen forceps.

2. A collagen forceps according to claim 1, wherein:

said channels are substantially hemispherical in cross-section.

3. A collagen forceps according to claim 1, wherein:

said distal portions of said first and second elongate members are angled at substantially a same angle and in substantially a same direction relative to said proximal portions of said first and second elongate members.

4. A collagen forceps according to claim 3, wherein:

said distal portions are angled approximately 15°–30° relative to said proximal portions.

5. A collagen forceps according to claim 1, further comprising:

d) a proximal shaft coupled to said coupling means.

6. A collagen forceps according to claim 5, wherein:

said shaft is angled in a first direction relative to said proximal portions of said first and second elongate members.

7. A collagen forceps according to claim 5, wherein:

said distal portions of said first ad second elongate members are angled in a second direction relative to said proximal portions of said first and second elongate members and said shaft.

8. A collagen forceps according to claim 1, wherein:

said first elongate member includes a first finger engagement means for receiving one of a finger or thumb of the practitioner, and said second elongate member includes a second finger engagement means for receiving the other of a finger or thumb of the practitioner, wherein the practitioner, by placement of his or her finger and thumb on said finger engagement means and by movement of his or her finger and thumb toward each other, is able to move said gripping means of said first elongate member toward said gripping means of said second elongate member.

9. A collagen forceps according to claim 1, wherein:

each of said first and second channels include a wall that contacts the collagen rod along more than two longitudinal lines parallel to the longitudinal axis of the collagen rod.

10. A collagen forceps having a longitudinal axis, said collagen forceps for use by a practitioner to insert a collagen rod having a longitudinal axis into a punctal opening of an eye, comprising:

a) a first elongate member having a proximal portion and distal portion;

b) a second elongate member having a proximal portion and a distal portion provided with a second end; and c) coupling means for hingeably coupling said first and second elongate members, at least one of said distal portions of said first and second elongate members having a first collagen rod gripping having a first channel, at least one of said distal portions of said first and second elongate members having a second collagen rod gripping means having a second channel angled relative to said first channel, each of said first and second collagen rod gripping means adapted to grip the collagen rod along more than two longitudinal lines parallel to the longitudinal axis of the collagen rod, wherein said collagen forceps in adapted to permit the practitioner to releasably securably grip the collagen rod within either of said first and second channels of said collagen forceps.

11. A collagen forceps according to claim 10, wherein:

said channel are substantially hemispherical in cross-section.

12. A collagen forceps according to claim 10, wherein:

said distal portions of said first and second elongate members are angled at substantially a same angle and substantially a same direction relative to said proximal portions of said first and second elongate members.

13. A collagen forceps according to claim 12, wherein:

said distal portions are angled approximately 15°–30° relative to said proximal portions.

14. A collagen forceps according to claim 10, further comprising:

d) a proximal shaft coupled to said coupling means.

15. A collagen forceps according to claim 14, wherein:

said shaft is angled in a first direction relative to said proximal portions of said first and second elongate members.

16. A collagen forceps according to claim 14, wherein:

said distal portions of said first and second elongate members are angled in a second direction relative to said proximal portions of said first and second elongate members and said shaft.

* * * * *